United States Patent [19]

Boberg et al.

[11] Patent Number: 4,808,724
[45] Date of Patent: Feb. 28, 1989

[54] 2-AMINOTHIAZOLYL-CONTAINING β-LACTAM ANTIBIOTICS

[75] Inventors: Michael Boberg; Karl G. Metzger, both of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 103,240

[22] Filed: Sep. 30, 1987

Related U.S. Application Data

[62] Division of Ser. No. 884,328, Jul. 10, 1986, Pat. No. 4,735,938.

[30] Foreign Application Priority Data

Jul. 2, 1982 [DE] Fed. Rep. of Germany ....... 3224866

[51] Int. Cl.[4] ......................................... G07D 277/40
[52] U.S. Cl. .................................................... 548/194
[58] Field of Search ........................................ 548/194

[56]   References Cited
   U.S. PATENT DOCUMENTS

| 4,405,617 | 9/1983 | Takaya | 544/27 |
| 4,735,938 | 4/1988 | Boberg | 514/206 |

Primary Examiner—Robert Gerstl
Attorney, Agent, or Firm—Sprung Horn Kramer & Woods

[57]   ABSTRACT

Antibiotically active penicillins and cephalosporins of the formula

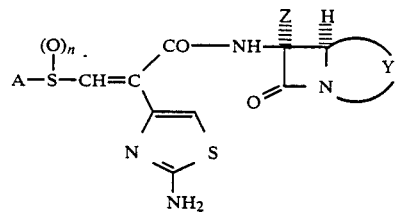

in which
Z is hydrogen or lower alkoxy,
n is 1 or 2,
Y, in the form of the free acid, is

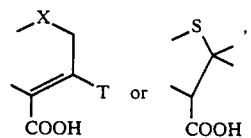

X is —S—, —n—, —SO— or —SO$_2$—,
T is an organic radical, hydrogen or halogen,
A is hydroxyl, optionally substituted alkyl, a substituted or unsubstituted phenyl ring, an optionally substituted polycyclic aromatic ring, an optionally substituted 5-membered or 6-membered heterocyclic ring with nitrogen, oxygen and/or sulphur as hetero atoms in the ring, or an optionally substituted polycyclic heterocyclic ring, or non-toxic pharmaceutically tolerated salts thereof.

1 Claim, No Drawings

2-AMINOTHIAZOLYL-CONTAINING β-LACTAM ANTIBIOTICS

This is a division of application Ser. No. 884,328, filed July 10, 1986 now U.S. Pat. No. 4,735,938.

The invention relates to β-lactam compounds, processes for their preparation and agents, such as medicaments, in particular antibacterial agents, and furthermore agents for promoting growth and for improving feed utilization in animals, as well as antioxidants.

β-Lactam compounds which carry a substituted acrylamido side chain have already been described.

Thus, for example, Belgian Patent Specification No. 633,397 and U.S. Pat. No. 3,622,569 mention penicillin compounds which contain the structural element

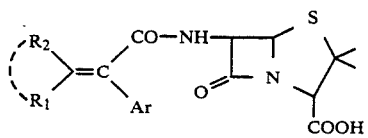

wherein
Ar can be a substituted phenyl ring or a heterocyclic structure and
$R^1$ and $R^2$ represent substituted or unsubstituted alkyl groups or a cycloalkyl group.

Furthermore, U.S. Pat. No. 4,014,869 describes cephalosporin compounds which have an acrylamido side chain which possesses a Z configuration and carries, inter alia, aromatic or heterocyclic radicals in the 2- and 3-position:

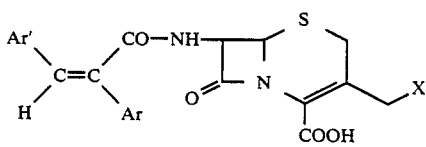

and Belgian Patent Specification No. 888,389 describes cephalosporin compounds which have an acrylamido side chain with aromatic or heterocyclic 2-substituents and alkylthio or alkoxy 3-substituents.

The present invention relates to β-lactam compounds corresponding to the general formula (I)

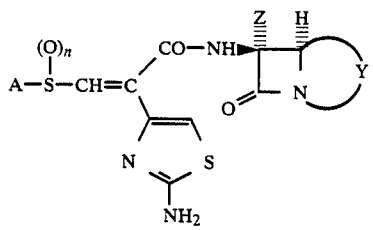

wherein, in the form of the free acid, Y denotes a radical of the formula IIa or IIb

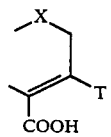

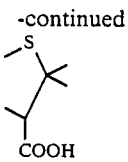

wherein
Z is hydrogen or lower alkoxy, ($C_1$-$C_6$, preferably $C_1$-$C_4$),
X is —S—, —O—, —SO— or —$SO_2$,
T is an organic radical, hydrogen or halogen, and
n is 1 or 2,
and wherein A denotes hydroxyl, optionally substituted alkyl, a substituted or unsubstituted phenyl ring, an optionally substituted polycyclic aromatic ring, an optionally substituted 5-membered or 6-membered heterocyclic ring with nitrogen, oxygen or sulphur as hetero atoms in the ring, or an optionally substituted polycyclic heterocyclic ring.

The invention furthermore relates to compounds corresponding to the general formula III

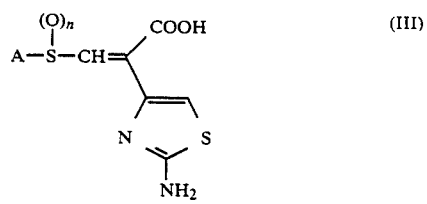

wherein A and n have the meaning given above.

The compounds according to the invention, of the formula (I), have very good antibacterial properties, and the compounds according to the invention, of the formula (III), serve as starting materials for the preparation of the compounds of the formula (I).

Corresponding to each structural formula, the compounds of the formulae (I) and (III) possess an E configuration and a Z configuration, in accordance with the E/Z nomenclature described in J. Amer. Chem. Soc. 90, 509 (1968).

Preferred compounds of the formulae (I) and (III) are present in the Z configuration.

The compounds of the formula (I) can be present as free acids, as esters, as inner salts or as non-toxic, pharmaceutically tolerated salts of the acific carboxyl groups, such as the sodium, potassium, magnesium, calcium, aluminum and ammonium salts, and non-toxic substituted ammonium salts, with amines, such as di- and tri-(lower alkyl)-amines, procaine, dibenzylamine, N,N'-dibenzylethylenediamine, N-benzyl-β-phenylethylamine, N-methyl- and N-ethylmorpholine, 1-ephenamine, dehydroabietylamine, N,N'-bis-dehydroabiethylethylenediamine, N-(lower alkyl)piperidine and other amines which can be used for the formation of salts of penicillins or cephalosporins.

When A represents an alkyl radical, this is preferably a straight-chain or branched, optionally substituted radial having up to 18 C atoms, particularly preferably having up to 12 C atoms, and specifically having up to 6 C atoms. Within the scope of this definition, alkyl is also intended to include unsaturated radicals and carbocyclic radicals.

Alkyl substituents are preferably halogen, preferably Cl, hydroxyl, lower alkoxy ($C_1-C_4$), an $OCOR^2$ group, thio, and

group, a

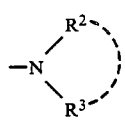

group, nitro, cyano, hydroxycarbonyl, lower alkoxycarbonyl ($C_1-C_4$), aminocarbonyloxy, sulpho or aryl, wherein in turn aryl denotes a substituted or unsubstituted carbocyclic aromatic ring or a 5-membered or 6-membered heterocyclic ring, and wherein $R^1$ denotes branched or straight-chain lower alkyl, preferably $C_1-C_4$, or optionally substituted aryl, wherein m can be 0, 1 or 2 and wherein $R^2$ and $R^3$ independently of one another can be hydrogen, or together or independently of one another can be lower alkyl, preferably $C_1-C_5$ or lower alkanoyl.

The meaning of alkyl also includes in each case substituted and/or cyclic and/or unsaturated structures, and preferably relates to radicals having 1–6 C atoms.

When A represents a phenyl radical, this is preferably a radical of the formula

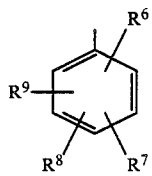

wherein $R^6$, $R^7$, $R^8$ and $R^9$ independently of one another denote hydrogen, halogen, preferably Cl, alkyl having up to 6 carbon atoms, aryl, a $—OCOR^{10}$ group,

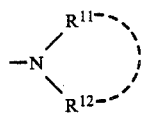

group, nitro, cyano, lower ($C_1-C_4$)-alkoxy, lower alkyl-($C_1-C_4$)-thio, hydroxycarbonyl, lower alkoxy-($C_1-C_4$)-carbonyl, aminocarbonyloxy, sulphonyl or sulpho,
wherein in turn aryl denotes a substituted or unsubstituted carbocyclic aromatic ring or a 5-membered or 6-membered heterocyclic ring,
and wherein $R^{10}$ denotes branched or straight-chain lower alkyl having up to 6 carbon atoms,
and wherein $R^{11}$ and $R^{12}$ independently of one another can be hydrogen, or together or independently of one another can be lower alkyl or lower alkanoyl, each having up to 6, preferably 4, C atoms in the alkyl part.

The meaning of alkyl also includes in each case substituted and/or cyclic and/or unsaturated structures.

When Y denotes a radical of the formula IIa, preferred compounds of the formula I are those in which Z denotes hydrogen or methoxy,
X denotes sulphur or oxygen and
T denotes hydrogen, $C_1-C_4$-alkyl, halogen, $C_1-C_4$-alkoxy, hydroxymethyl, formyloxymethyl, $C_1-C_4$-alkylcarbonyloxymethyl, aminocarbonyloxymethyl, pyridiniummethyl, 4-carbamoylpyridiniummethyl, halogenomethyl or chloromethyl, dichloroacetoxymethyl, sulphonyloxymethyl or heterocyclylthiomethyl, heterocyclyl preferably representing a radical of the formula

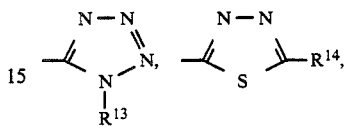

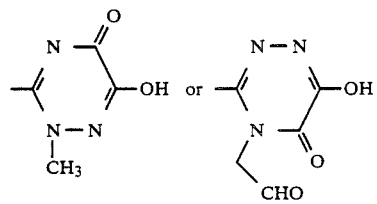

wherein
$R^{13}$ denotes hydrogen, methyl, 2-dimethylaminoethyl, sulphoaminoethyl, carboxymethyl or sulphomethyl and
$R^{14}$ denotes hydrogen or methyl.

Particularly preferred compounds with the Z configuration are those of the formula I in which Y has the meaning IIb or IIa,
wherein
Z denotes hydrogen or methoxy,
X denotes sulphur,
T denotes hydrogen, halogen or a radical

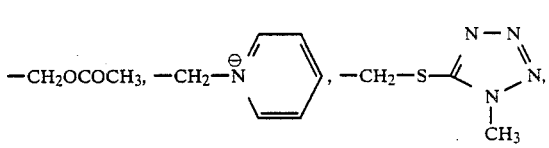

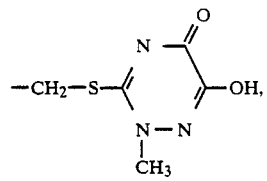

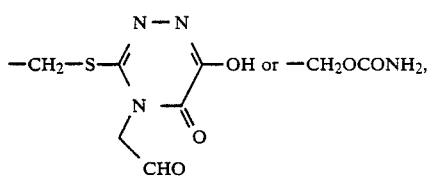

and in which
n is 2, and
A denotes hydroxyl, lower alkyl having up to 6 carbon atoms or aryl, wherein aryl denotes an unsubstituted or substituted phenyl radical, where in turn preferred substituents are halogen, lower alkyl having up to 6 carbon atoms, lower alkoxy or hydroxycarbonyl.

The meaning of lower alkyl includes in each case acyclic, cyclic, saturated and unsaturated structures.

The particular Z and E forms of the same structural formula are as a rule substances which possess different activities and which can be prepared separately from one another or together.

The compounds of the general formula I can be obtained by a process in which compounds which are of the general formula III

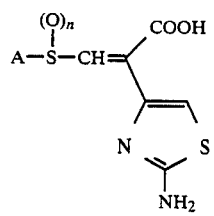

wherein A and n have the meaning given above, and in which the amino group can be present in a protected or unprotected form, after activation of the carboxyl group by conversion to a mixed anhydride, for example with ethyl chloroformate or methanesulphonyl chloride, after conversion to the acid-halide or after conversion to an activated ester with, for example, N-hydroxysuccinimide and dicyclohexylcarbodiimide, are brought to reaction with compounds which can also be present in the mono- or disilyl form and in which the carboxyl group can be present in a protected or unprotected form, of the general formula IV

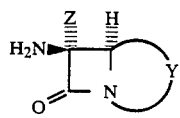

wherein Y and Z have the abovementioned meaning, and then, if appropriate, the protective groups are split off, and the desired salts are prepared, or the free acids are prepared from salts.

The compounds according to the invention, of the formula (I) with Y=IIa, can also be obtained by reacting compounds of the formula (I) and Y=IIa, in which T has the meaning of —CH$_2$—O—CO—(lower alkyl), in particular —CH$_2$—OCOCH$_3$, or halogenomethyl, sulphonyloxymethyl or dichloroacetoxymethyl, with nucleophiles, for example

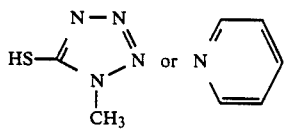

Compounds of the formula (I) are furthermore obtained when compounds of the general formula (I) and Y=IIa, in which T has the meaning of CH$_2$OH, are reacted with O=C=NSO$_2$Cl or O=C=N—COCCl$_3$, and the SO$_2$Cl— or —COCCl$_3$ group is then split off.

Compounds of the formula (I) in which Z denotes alkoxy can also be obtained when compounds of the formula (I) in which Z denotes hydrogen and which are present in the form of the free acids, the salts or cleavable esters, are reacted with a hypochlorite, for example (CH$_3$)$_3$COCl, in the presence of an alcoholate, preferably a methylate, for example LiOCH$_3$, and, if appropriate, protective groups are removed.

The compounds of the general formula (III) can be obtained when compounds of the general formula V

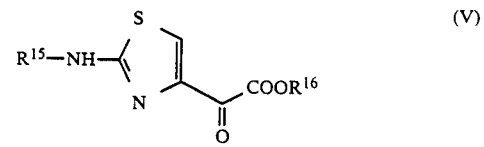

wherein R$^{15}$ denotes an amine protective group, such as, for example, tert.-butoxycarbonyl, triphenylmethyl, formyl or 2-trimethylsilylethoxycarbonyl, and wherein R$^{16}$ denotes optionally substituted, branched or straight-chain lower alkyl, are reacted with a phosphonate of the general formula (VI)

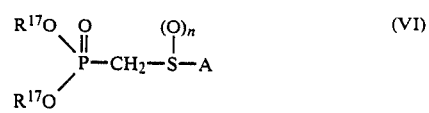

wherein

A and n have the abovementioned meaning, and

R$^{17}$ denotes lower alkyl having up to 6 C atoms or aryl, preferably methyl, ethyl, isopropyl or phenyl, and the ester COOR$^{16}$ is then cleaved, and if appropriate the protective group R$^{15}$ is also split off. Preferred compounds of the formula (V) are those in which R$^{15}$ denotes tert.-butoxycarbonyl or 2-trimethylsilylethoxycarbonyl and R$^{16}$ denotes methyl, ethyl, tert.-butyl, 2-trimethylsilylethyl or diphenylmethyl.

The compounds according to the invention exhibit a broad antibacterial spectrum against Gram-positive and Gram-negative germs, in particular against Enterobacteriaceae, above all against those with β-lactamase formation.

Furthermore, the compounds according to the invention improve the growth and feed utilization in animals and can be used as antioxidants.

The compounds according to the invention display a powerful and broad antimicrobial activity, coupled with low toxicity. These properties enable them to be used as chemotherapeutic active compounds in medicine and as substances for preserving inorganic and organic materials, especially organic materials of all kinds, for example polymers, lubricants, paints, fibers, leather, paper and timber, and foodstuffs and water.

The compounds according to the invention are active against a very broad spectrum of micro-organisms. With their aid, Gram-negative and Gram-positive bacteria and bacteria-like micro-organisms can be combated, and diseases caused by these pathogens can be prevented, alleviated and/or cured.

The compounds according to the invention are particularly active against bacteria and bacteria-like micro-organisms. They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus* and *Staph. epidermidis* (Staph.=Staphylococcus); Lactobacteriaceae, such as Streptococci, for example *Streptococcus pyogenes*, α- and β-haemolysing Streptococci and non-(γ-)-haemolysing Streptococci, Enterococci and *Dipolococcus pneumoniae* (Pneumococci) (Str.=Streptococcus); Enterobacteriaceae, such as Escherichiae bacteria of the *Coli* group: Escherichia bacteria, for example *Escherichia coli*, Enterobacter bacteria, for example *E. aerogenes* and *E. cloacae*, Klebsiella bacteria, for example *K. pneumoniae*, and Serratia, for example *Serratia marcescens* (E.=Enterobacter) (K.=Klebsiella), Proteae bacteria of the Proteus group: Proteus, for example *Proteus vulgaris, Pr. morganii, Pr. rettgeri* and *Pr. mirabilis* (Pr.=Proteus);

Pseudomonadaceae, such as Pseudomonas bacteria, for example *Pseudomonas aeruginosa* (PS.=Pseudomonas);

Bacteroidaceae, such as Bacteroides bacteria, for example *Bacteroides fragilis* (B.=Bacteroides).

The above list of pathogens is purely illustrative and is in no way to be interpreted as restrictive.

Examples which may be mentioned of diseases which can be prevented, alleviated and/or cured by the compounds according to the invention are: diseases of the respiratory passages and of the pharyngeal cavity; otitis; pharyngitis; pneumonia; peritonitis; pyelonephritis; cystitis; endocarditis; systemic infections; bronchitis; arthritis; and local infections.

The present invention includes pharmaceutical formulations which, in additiion to non-toxic, inert pharmaceutically suitable excipients, contain one or more compounds according to the invention, or which consist of one or more active compounds according to the invention, as well as processes for the preparation of these formulations.

The present invention also includes pharmaceutical formulations in dosage units. This means that the formulation are in the form of individual parts, for example tablets, dragees, capsules, pills, suppositories and ampoules, of which the content of active compound correspond to a fraction or a multiple of an individual dose. The dosage units can contain, for example, 1, 2, 3 or 4 individual or $\frac{1}{2}$, $\frac{1}{3}$ or $\frac{1}{4}$ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl acohols, polyoxyethylene sorbitol esters and sorbitan esters, micro-crystalline cellulose, aluminum metahydroxide, bentonite, agar-agar and tragacanth, or mixtures of these substances.

The formulation forms mentioned can also contain colorants, preservatives and additives which improve the odor and flavor for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, percent by weight of the total mixture.

The abovementioned pharmaceutically active compounds can also contain other pharmaceutical active compounds in addition to the compounds according to the invention.

The abovementioned pharmaceutical formulations are prepared in the customary manner according to known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general, it has proved advantageous both in human medicine and in veterinary medicine, to administer the active compound or compounds according to the invention in total amounts of about 5 to about 1,000, preferably 10 to 200, mg/kg of body weight every 24 hours, optionally in the form of several individual administrations, in order to achieve the desired results. An individual administration preferably contains the active compound or compounds according to the invention in amounts of about 1 to about 250, in particular 3 to 60, mg/kg of body weight. However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, while in other cases the abovementioned amount of active compound must be exceeded. The particular optimum dosage required and the type of administration of the active compounds can easily be determined by anyone skilled in the art on the basis of his expert knowledge.

When used as feed additives, the new compounds can be administered in the customary concentrations and formuations together with the feed or with the feed formulations or with the drinking water. By this means, it is possible to prevent, alleviate and/or cure an infection by Gram-negative to Gram-positive bacteria and also to achieve promotion of growth and better utilization of the feed.

The new compounds are distinguished by powerful antibacterial actions, which have been tested in vivo and in vitro, and can be absorbed after oral administration.

In order to broaden the spectrum of action and to achieve a more powerful action especially in the case of β-lactamase-forming bacteria, the compounds according to the invention can be combined with other antimicrobial active compounds, for example with penicillins or other beta-lactams which are particularly resistant to penicillinase. An example of such a combination is that with oxacillin or dicloxacillin.

In order to broaden the spectrum of action and to achieve a more powerful action, the compounds according to the invention can also be combined with aminoglycoside antibiotics, such as, for example, gentamicin, sisomicin, kanamicin, amikacin or tobramicin.

The compounds according to the invention prevent the degradation of, for example, penicillins by β-lactamases which normally hydrlyze sensitive penicillins and hence render them inactive.

The activity of the β-lactam antibiotics according to the invention can be demonstrated, by way of example, by the following in vitro experiments:

In vitro experiments

The compounds from Examples 5 and 10, which can be regarded as typical representatives of the compounds according to the invention, were tested in respect of antibacterial action, in an agar dilution test under German DIN conditions. The concentration was 100 mcg per milliliter of agar. Complete inhibition of growth was found in the case of the following strains of bacteria:

*E. coli* Neumann, Klebsiella 63, *Serratia marcescens* 16001, Providencia 12012, *Proteus morganii* 11006, *Proteus vulgaris* 1017, *Proteus rettgeri*, *Pseudomonas aeruginosa* W, *Bacteroides fragilis* 012,999, *Staphylococcus aureus* 133 and Enterococcus ATCC 9790.

Preparation of the novel compounds is illustrated in the following examples wherein the termperatures are in °C.

EXAMPLE 1

Ethyl 2-(2-tert.-butoxycarbonylaminothiazol-4-yl)-3-methylsulphonyl propenoate

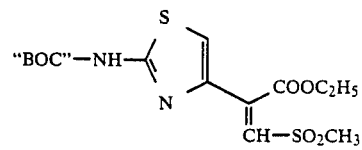

"BOC" = tert.-butoxycarbonyl 71 ml of a 1.5 normal solution of n-butyl-lithium in hexane are added dropwise to a stirred solution of 23 g of diethyl methylsulphonylmethyl phosphonate in 500 ml of absolute tetrahydrofuran at −78°, under a stream of nitrogen, in a heated flask. Thereafter, a solution of 30 g of ethyl 2-(2-tert.-butoxycarbonylaminothiazol-4-yl)-2-oxo-acetate in 300 ml of absolute tetrahydrofuran is added dropwise, and the mixture is stirred for a further 4 hours. The solution is allowed to reach room temperature slowly and is then poured onto ice/water, the pH is adjusted to 6, and the tetrahydrofuran is stripped off. The aqueous phase is extracted three times with ethyl acetate, and the combined organic phases are dried and evaporated down. Crude yield 46.0 g. Chromatography over an 80-fold amount of silica gel (mobile phase toluene/ethyl acetate: 4/1) gives 9 g of a 1:1 mixture of the Z-isomer (non-polar product) and the starting material, 17.2 g of the pure Z-isomer and 1.6 g of the pure E-isomer (polar product). Yield: 53.2%.

Z-Isomer

IR (methylene chloride): 1715, 1590, 1545, 1440, 1370, 1350, 1310, 1225, 1200, 1140 cm$^{-1}$.

NMR (CDCl$_3$): δ=7.12(1)s, 7.09(1)s, 4.42(1)g, J=7 Hz, 3.08(3)s, 1.57(9)s, 1.41(3)t, J=7 Hz ppm.

E-Isomer

IR (CH$_2$Cl$_2$): 1715, 1540, 1440, 1420, 1365, 1310, 1230, 1145 cm$^{-1}$.

NMR (CDCl$_3$): δ=7.42(1)s, 7.21(1)s, 4.26(2)q, J=7 Hz, 3.04(3)s, 1.52(9)s, 1.31(3)t, J=7 Hz ppm.

EXAMPLE 2

2-Trimethylsilylethyl 2-(2-tert.-butoxycarbonylaminothiazol-4-yl)-3-methylsulphonyl propenoate

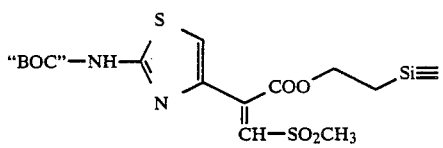

55.94 ml of a 1.5M solution of n-butyl-lithium in hexane are added dropwise to a solution of 8.64 ml of diisopropylamine in 120 ml of absolute tetrahydrofuran at −70°, under nitrogen, in a heated flask. After 15 minutes, 17.3 g of diethyl methylsulphonylmethyl phosphonate are added, and after a further 15 minutes a solution of 30 g of 2-trimethylsilyl ethyl 2-(2-tert.-butoxycarbonylaminothiazol-4-yl)-2-oxoacetate in 50 ml of absolute tetrahydrofuran is added dropwise. The reaction mixture is kept at −40° for one hour, and is then thawed at room temperature and stirred further overnight. Working up as in Example 1 gives 40.3 g of crude product, which is processed further without purification. According to thin layer chromatography/NMR, one isomer is formed in excess.

NMR (CDCl$_3$): δ=7.16(1)s, 7.12(1)s, 4.45(2)m, 3.10(3)s,

Principal product 1.52(9)s, 1.22(2)m, 0.03(9)s ppm.

EXAMPLE 3

Z-2-(2-tert.-butoxycarbonylaminothiazol-4-yl)-3-methylsulphonyl propenoic acid

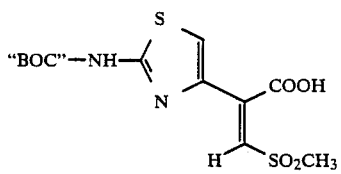

10.3 g of the pure Z-isomer prepared according to Example 1 are dissolved in 50 ml of ethanol. 60 ml of 1N sodium hydroxide solution are added, and the mixture is stirred overnight at room temperature. After the alcohol has been stripped off, the aqueous solution, at pH 9.5, is extracted three times with ethyl acetate, adjusted to pH 2.5, and again extracted three times with ethyl acetate. These last combined extracts are dried over magnesium sulphate and evaporated down. Crystallization from toluene gives a pure product. Mp. 135°–40° (decomposition), yield 28.2%.

200 ml of a 1M solution of tetrabutylammonium fluoride in tetrahydrofuran are added to a solution of 40.3 g of the product from Example 2 in 200 ml of absolute tetrahydrofuran. After the mixture has stood for one hour at room temperature, the tetrahydrofuran is stripped off, the residue is dissolved in ethyl acetate, and this solution is extracted three times with 1N sulphuric acid and once with water. Drying, evaporating down and crystallization with toluene give a product which is a pure isomer, as above. Mp 141.5 (decomposition), yield 28.1% over 2 stages.

IR (Nujol): 1725, 1595, 1550, 1460, 1370, 1305, 1235, 1200, 1150, 1120, 1080 cm$^{-1}$.

NMR (CDCl$_3$): δ=9.25(2)s broad, 7.45(1)s, 7.27(1)s, 7.23(1)s, 3.23(3)s, 1.60(9)s ppm.

Calculated for 1 mmol of product+½ mol of toluene: C: 47.2, H: 5.1, N: 7.1, S: 16.2, Found: C: 48.0, H: 5.2, N: 7.2, S: 15.8.

EXAMPLE 4

Tert.-butyl 7-(2-(2-tert.-butoxycarbonylaminothiazol-4yl)-3-methylsulphonylprop-2-enoyl)amino-3-acetoxymethyl-3-cephem-4-carboxylate

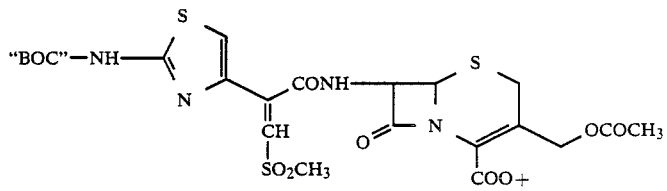

2 g of the acid prepared according to Example 3 are dissolved with 0.71 ml of triethylamine in 200 ml of methylene chloride, under nitrogen, in a heated apparatus. The solution is cooled to −60°, 0.39 ml of methanesulphonyl chloride is added and the mixture is stirred for a further two hours. 1.66 g of tert.-butyl 7-aminocephalosporanate, dissolved in 200 ml of methylene chloride, are then added. The reaction mixture is allowed to thaw slowly at room temperature, and is stirred further overnight.

The solvent is evaporated off without heating, the residue is taken up in ethyl acetate, and the organic phase is washed three times with 1N hydrochloric acid, once with water, twice with saturated sodium bicarbonate solution and once again with water, in succession, and is dried and evaporated down. 1.4 g of a yellow foam remain, which according to thin layer chromatography and the NMR spectrum represents the desired Z-isomer in about 90% purity, and can therefore be employed in the next reaction without further purification; crude yield 39.6%. To achieve higher purity, a chromatographic procedure is required.

If the activation is carried out at −20° instead of at −60°, equilibrium of the double bond gives a ∼1:1 E/Z mixture, which can be separated by chromatography (0.9 g over 80 g of silica gel 60, 230–400 mesh, Merck, mobile phase methylene chloride/methanol 94/4).

Z-Isomer

IR (CHCl$_3$): 1786, 1727, 1685, 1551, 1372, 1318, 1208, 1155 cm$^{-1}$.

NMR (CDCl$_3$): δ=9.10(1)s, 7.80(1)d, J=8 Hz, 7.27(1)s, 7.09(1)s, 6.02(1)dd, J=8 Hz, 5.08(1)d, J=5 Hz, 5.10(1)d, J=23 Hz, 4.81(1)d, J=13 Hz, 3.59(1), J=18 Hz, 3.41(1)d, J=18 Hz, 3.12(3)s, 2.10(3)s, 1.55(9)s, 1.53(9)s ppm.

E-Isomer

IR (CHCl$_3$): 1775, 1722, 1676, 1551, 1395, 1371, 1313, 1251, 1206, 1152 cm$^{-1}$.

NMR (CDCl₃): δ=10.82(1)s broad, 8.15(1)d, J=8 Hz, broad, 7.81(1)s, 7.52(1)s, 5.43(1)dd, J=8 Hz, J=5 Hz, 4.88(1)d, J=5 Hz, 5.21(1)d, J=13 Hz, 4.67(1)d, J=13 Hz, 3.50(1)d, J=28 Hz, 3.35(1)d, J=18 Hz, 2.94(3)s, 2.07(3)s, 1.55(9)s, 1.45(9)s ppm.

EXAMPLE 5

7-(2-(2-aminothiazol-4-yl)-3-methylsulphonylprop-2-enoyl)amino-3-acetoxymethyl-3-cephem-4-carboxylic acid trifluoroacetate

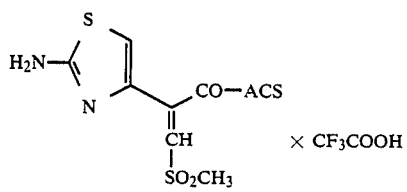

1. Z-Isomer 0.8 g of the Z-isomer prepared in Example 4 is dissolved in 10 ml of trifluoroacetic acid at 0°, under nitrogen. The mixture is allowed to reach room temperature, and after one hour is evaporated down without heating. The residue is stirred with twice 50 ml of methylene chloride, and the solution is evaporated down again. Crystallization with ether gives the pure product. Yield 0.8 g.

IR (KBr): 1781, 1728, 1653, 1542, 1381, 1316, 1261, 1198, 1133, 1102, 1024 cm⁻¹.

NMR (CD₃OD): δ=7.02(1)s, 5.89(1)d, J=5 Hz, 5.18(1)d, J=5 Hz, 5.11(1)d, J=13 Hz, 4.81(1)d, J=12 Hz, 3.70(1)d, J=18 Hz, 3.47(1)d, H=18 Hz, 3.10(3)s, 2.03(3)s ppm.

2. E-Isomer

The pure E-isomer prepared according to Example 4 is converted to the title compound, as described under 1.

IR (KBr): 1782, 1729, 1670, 1532, 1383, 1313, 1263, 1199, 1140, 1027 cm⁻¹.

NMR (CD₃OD): δ=7.39(1)s, 7.14(1)s, 5.81(1)d, J=5 Hz, 5.13(1)d, J=5 Hz, 5.08(1)d, J=13 Hz, 4.81(1)d, J=13 Hz, 3.68(1)d, J=18 Hz, 3.46(1)d, J=18 Hz, 3.15(3)s, 2.03(3)s ppm.

EXAMPLE 6

Tert.-butyl Z-7-(2-(β-tert.-butoxycarbonylaminothiazol-4-yl)-3-methylsulphonylprop-2-enoyl)-amino-3-(1-methyl-1-H-tetrazol-5-yl)thiomethyl-3-cephem-4-carboxylate

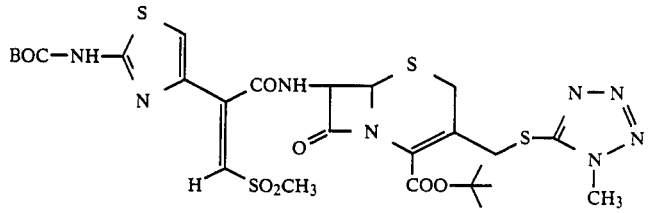

1 g of the acid prepared in Example 3 is reacted, analogously to Example 4, with tert.-butyl 7-amino-3-(1-methyl-1-H-tetrazol-5-yl)-thiomethylcephalosporanate instead of tert.-butyl 7-aminocephalosporanate. 1 g of crude product, which can be used further without purification, is obtained.

IR (KBr): 1782, 1715, 1540, 1452, 1366, 1243, 1152, 1133 cm⁻¹.

NMR (CDCl₃): δ=8.47(1)s, broad, 7.25(1)s, 7.23(1)d, J=8 Hz, 7.05(1)s, 6.02(1)dd, J=8 Hz, J=5 Hz, 5.09(1)d, J=5 Hz, 4.45(1)d, J=13 Hz, 4.34(1)d, J=13 Hz, 3.94(3)s, 3.72(2)s, 3.11(3)s, 1.56(18)s ppm.

EXAMPLE 7

Z-7-(2-(2-Aminothiazol-4-yl)-3-methylsulphonylprop-2-enoyl)-amino-3-(1-methyl-1-H-tetrazol-5-yl)thiomethyl-3-cephem-4-carboxylic acid trifluoroacetate

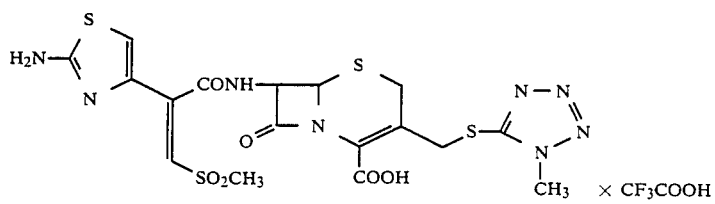

When the product prepared in Example 6 is treated with trifluoroacetic acid as described in Example 5, the title compound is obtained.

NMR (CD₃OD): δ=7.03(1)s, 7.02(1)s, 5.87(1)d, J=5 Hz, 5.81(1)d, J=5 Hz, 4.39(1)d, J=15 Hz, 4.26(1)d, J=15 Hz, 4.00(3)s, 3.85(1)d, J=18 Hz, 3.70(1)d, J=18 Hz, 3.12(3)s ppm.

EXAMPLE 8

Diphenylmethyl 2-(2-tert.-butoxycarbonylaminothiazol-4-yl)-3-methylsulphonyl propenoate

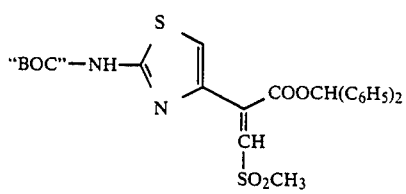

8.8 g of diethyl methylsulphonylmethyl phosphonate are reacted with 18 g of diphenylmethyl 2-(2-tert.-butoxycarbonylaminothiazol-4-yl)-2-oxoacetate, analogously to Example 2. 9.2 g of the polar isomer are separated off from the crude product by crystallization with ether. After the mother liquor has been evaporated down, 11.2 g of the slightly contaminated non-polar isomer remain as a viscous oil. Yield 95%.

Polar isomer Mp. 191° (decomposition).

IR (Nujol): 1720, 1600, 1560, 1460, 1370, 1315, 1285, 1240, 1190, 1160, 1134, 1080, 960 cm$^{-1}$.

NMR (CDCl$_3$): δ=8.20(1) broad, 7.43(10)s, 7.32(1)s, 7.18(1)s, 6.69(1)s, 2.94(3)s, 1.56(9)s ppm.

Non-polar isomer

NMR (CDCl$_3$): δ=7.31(13)m, 3.03(3)s, 1.49(9)s ppm.

EXAMPLE 9

2-(2-Aminothiazol-4-yl)-3-methylsulphonyl propenoic acid

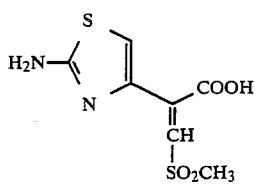

16 g of the crystalline isomer prepared in Example 8 are introduced into a stirred solution of 10.8 g of anisole in 200 ml of trifluoroacetic acid, at 0°, under a nitrogen atmosphere. The clear solution is allowed to reach room temperature, is stirred for a further hour and is evaporated down without heating. The residue is taken up in twice 200 ml of methylene chloride, and the solution is evaporated down again. Ethyl acetate and water are added, and the pH is adjusted to 8 with 2N sodium hydroxide solution. After the organic phase has been separated off, the aqueous phase is washed twice with ethyl acetate, ethyl acetate is then added, and the pH is reduced to 2 by the addition of 2N hydrochloric acid. The precipitated product is filtered off under suction, and recrystallized from acetonitrile. Yield 54.4%, Mp. 181° (decomposition).

IR (Nujol): 1665, 1600, 1580, 1315, 1295, 1260, 1130, 970 cm$^{-1}$.

NMR (DMSO): δ=7.34(2)s, 6.95(1)s, 6.87(1)s, 3.12(3)s ppm.

Calculated: C: 33.9, H: 3.2, N: 11.3, S: 25.8, Found: C: 33.9, H: 3.4, N: 11.6, S: 23.9.

EXAMPLE 10

Sodium 6-(2-(2-aminothiazol-4-yl)-3-methylsulphonyl-propenoyl)-aminopenam-3-carboxylate

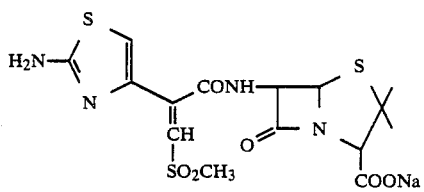

0.4 ml of methanesulphonyl chloride is added to a solution of 1 g of the product prepared according to Example 9 and 1.2 ml of tributylamine in 50 ml of absolute methylene chloride at −50°, under a nitrogen atmosphere. The mixture is stirred for a further 24 hours at −78°, and a solution of 1.2 g of 6-aminopenicillanic acid and 1.5 ml of triethylamine in 50 ml of methylene chloride is then added dropwise. After one hour, the solution is thawed out, stirred for a further 20 hours at room temperature and then evaporated down without heating. The residue is taken up in water, and the solution is adjusted to pH 2.8 and extracted three times with ethyl acetate. The combined organic phases are washed with water, water is then added, and the pH is slowly adjusted to 7.0 with 2N sodium hydroxide solution. After the organic phase has been separated off, 0.8 g of the desired product is obtained as an isomer mixture by freeze-drying the aqueous solution.

IR (Nujol): 1780, 1650, 1600, 1540, 1305, 1135, 975 cm$^{-1}$.

NMR (DMSO): δ=9.26/9.58(1)d, J=6 Hz, 7.33(2)s broadened, 6.98(1)s, 6.87/6.82(1)s, 5.54(2)m, 4.25/4.24(1)s, 3.14/3.12(3)s, 1.58(3)s, 1.48(3)s ppm.

EXAMPLE 11

2-Trimethylsilylethyl 2-(2-tert.-butoxycarbonylaminothiazol-4-yl)-3-phenyl-sulphonyl propenoate

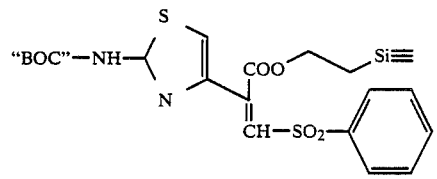

16.0 g of diethyl phenylsulphonylmethyl phosphonate are reacted with 20.4 g of 2-trimethylsilylethyl 2-(2-tert.-butoxycarbonylaminothiazol-4-yl)-2-oxoacetate, analogously to Example 2. 32.6 of an oily crude product are obtained, from which 7.8 g of the non-polar Z-isomer and 5.2 g of the polar E-isomer are separated off by chromatography over silica gel (mobile phase toluene/ethyl acetate: 7/1).

Z-Isomer

NMR (DMSO): δ=11.74[1]S, 7.95[2]m, 7.70[3]m, 7.57[1]s, 7.03[1]s, 4.43[2]m, 1.43[9]s, 1.11[2]m, 0.02[9]s ppm.

E-Isomer

NMR (DMSO): δ=11.51[1]s, 7.85[2]m, 7.55–7.80[3]m, 7.45[1]s, 7.36[1]s, 4.21[2]m, 1.49[9]s, 0.92[2]m, −0.05[9]s ppm.

EXAMPLE 12

2-(2-Tert.-butoxycarbonylaminothiazol-4-yl)-3-phenyl-sulphonyl propenoic acid

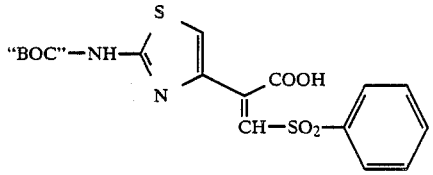

7.2 g of the Z-isomer prepared according to Example 11 are dissolved in 28.8 ml of a 1-N solution of tetrabutylammonium fluoride in tetrahydrofuran, at room temperature. The solution is stirred overnight, and is then worked up as described in Example 3.

Crystallization with ether gives 5.1 g of the acid in the form of the pure Z-isomer. Mp. 194° (decomposition).

IR (Nujol): 1700, 1600, 1555, 1300, 1280, 1239, 1140, 1072 cm$^{-1}$.

NMR (DMSO): =11.74[1]s, 7.98[2]m, 7.70[3]m, 7.55[1]s, 6.96[1]s, 1.47[9]s ppm.

In the same manner, the E-carboxylic acid is prepared from the E-isomer produced according to Example 11.

IR (CHCl$_3$): 1710, 1540, 1440, 1360, 1295, 1223, 1141, 1074 cm$^{-1}$.

NMR (DMSO): δ=11.52[1]s, 7.87[2]m, 7.55-7.80[3]m, 7.45[1]s, 7.32[1]s, 1.50[9]s ppm.

EXAMPLE 13

Tert.-butyl 7-(2-(2-tert.-butoxycarbonylaminothiazol-4-yl)-3-phenylsulphonylprop-2-enoyl)amino-3-acetoxymethyl-3-cephem-4-carboxylate

EXAMPLE 14

Sodium 7-(2-(2-aminothiazol-4-yl)-3-phenylsulphonylprop-2-enoyl)amino-3-acetoxymethyl-3-cephem-4-carboxylate

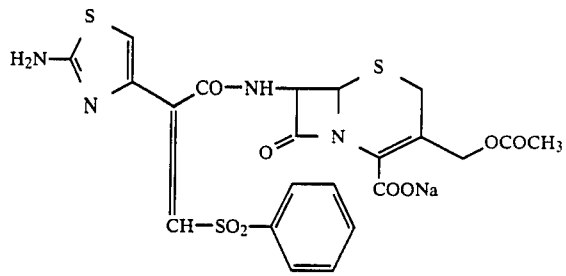

1. Z-Isomer 1.5 g of the Z-isomer prepared according to Example

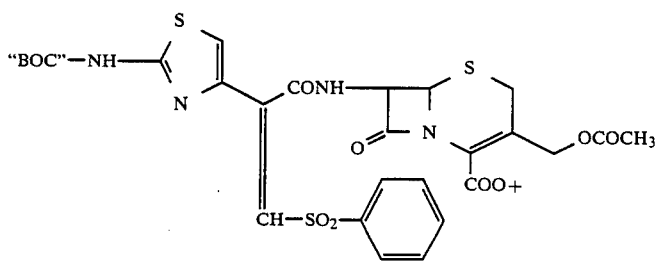

1.25 g of the Z-isomer prepared according to Example 12 are reacted with tert.-butyl 7-aminocephalosporanate, according to the instructions of Example 4. 1.6 g of a yellow foam are obtained, which is reacted without further purification.

IR (CHCl$_3$): 1779, 1715, 1540, 1360, 1300, 1218, 1141 cm$^{-1}$.

NMR (DMSO): =9.88[1]d, J=7 Hz, 8.02[2]d, J=7 Hz, 7.60-7.84[3]m, 7.34[1]s, 6.88[1]S, 5.96[1]dd, J=7 Hz, J=5 Hz, 5.30[1]d, J=5 Hz, 4.98[1]d, J=13 Hz, 4.66[1]d, J=13 Hz, 3.70[1]d, J=17 Hz, 3.54[1]d, J=17 Hz, 2.06[3]s, 1.51[9]s, 1.49[9]s ppm.

1.25 g of the E-isomer prepared according to Example 12 are reacted analogously:

IR(KBr): 1778, 1721, 1675, 1544, 1447, 1392, 1369, 1250, 1153 cm$^{-1}$.

NMR (DMSO): δ=11.60[1]s, 9.54[1]d, J=7 Hz, 7.92[2]d, J=7 Hz, 7.55-7.80[3]m, 7.48[1]s, 7.10[1]s, 5.71[1]dd, J=7 Hz, J=5 Hz, 5.18[1]d, J=5 Hz, 4.92[1]d, J=13 Hz, 4.64[1]d, J=13 Hz, 3.69[1]d, J=17 Hz, 3.42[1]d, J=17 Hz, 2.05[3]s, 1.49[9]s ppm.

13 are dissolved in 50 ml of trifluoroacetic acid, at 0° C. After the solution has been stirred for one hour at room temperature, it is evaporated down without heating, 50 ml of absolute methylene chloride are added to the residue, and the mixture is evaporated down again. The residue is then dissolved in 10 ml of water and pH 7, with the addition of 2N sodium hydroxide solution, and the solution is extracted three times with ethyl acetate. The free acid is precipitated at pH 3.0 by the addition of 2N hydrochloric acid, and is filtered off under suction, and the residue is suspended in water, and brought into solution again, at pH 7.0, by the addition of 2N sodium hydroxide solution. Lyophilization of the aqueous phase gives 1 g of product.

IR (Nujol): 1780, 1675, 1605, 1530, 1300, 1230, 1150, 1090, 1030 cm$^{-1}$.

NMR (CD$_3$OD): δ=8.03[2]d, J=6 Hz, 7.62[3]m, 6.98[1]s, 6.95[1]s, 5.87[1]d, J=5 Hz, 5.17[1]d, J=5 Hz, 5.01[1]d, J=13 Hz, 4.81[1]d, J=13 Hz, 3.64[1]d, J=18 Hz, 3.35[1]d, J=18 Hz, 2.03[3]s ppm.

2. E-Isomer

In the same manner, the E-isomer of the title compound is obtained from the E-isomer of Example 13.

IR (Nujol): 1760, 1720, 1603, 1300, 1240, 1150, 1075, 1028 cm$^{-1}$.

NMR (CD$_3$OD): δ=7.83[2]m, 7.50-7.72[3]m, 7.32[1]s, 7.08[1]s, 5.71[1]d, J=5 Hz, 5.05[1]d, J=5 Hz, 4.99[1]d, J=13 Hz, 4.82[1]d, J=13 Hz, 3.59[1]d, J=17 Hz, 3.32[1]d, J=17 Hz, 2.04[3] s ppm.

EXAMPLE 15

2-Trimethylsilylethyl 2-(2-tert.-butoxycarbonylaminothiazol-4-yl)-3-methyl-sulphinyl-propenoate

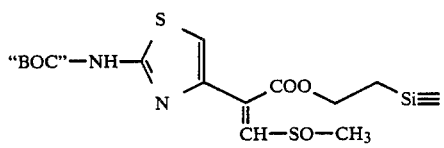

5.25 g of diethyl methylsulphinylmethyl phosphonate are reacted with 7.4 g of 2-trimethylsilylethyl 2-(2-tert.-butoxycarbonylaminothiazol-4-yl)-2-oxoacetate, analogously to Example 2. Chromatography of the crude product over silica gel (mobile phase toluene/ethyl acetate: 4/1) gives 3 g of the Z-isomer and 2.8 g of the E-isomer.

Z-Isomer

NMR (DMSO): δ=11.71[1]s, 7.47[1]s, 7.31[1]s, 4.35[2]m, 2.78[3]s, 1.48[9]s, 1.09[2]m, 0.03[9]s ppm.

E-Isomer

NMR (DMSO): δ=11.66[1]s, 7.62[1]s, 7.13[1]s, 4.32[2]m, 2.87[3]s, 1.50[9]s, 1.07[2]m, 0.03[9] ppm.

EXAMPLE 16

2-(2-Tert.-butoxycarbonylaminothiazol-4-yl)-3-methyl-sulphinyl-propenoic acid

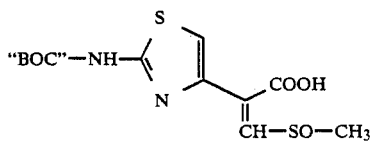

The esters prepared according to Example 15 and obtained as pure isomers are reacted separately, according to Example 12, and the mixture is worked up.

E-Isomer

Mp.: 182° (decomposition) (ether).

IR (KBr): 1722, 1546, 1453, 1393, 1366, 1279, 1245, 1155, 1127, 1077 cm$^{-1}$.

NMR (DMSO): δ=10.02[1]s, 7.64[1]s, 7.18[1]s, 2.90[3]s, 1.50[9].

Z-Isomer

Mp.: 169° (decomposition) (methylene chloride).

IR (KBr): 1720, 1560, 1454, 1370, 1246, 1154, 1075 cm$^{-1}$.

NMR (DMSO): 9.94[1]s, 7.50[1]s, 7.28[1]s, 2.73[3]s, 1.49[9]s ppm.

EXAMPLE 17

Tert.-butyl E-7-(2-2-tert.-butoxycarbonylaminothiazol-4-yl)-3-methylsulphinylprop-2-enoyl)amino-3-acetoxymethyl-3-cephem-4-carboxylate

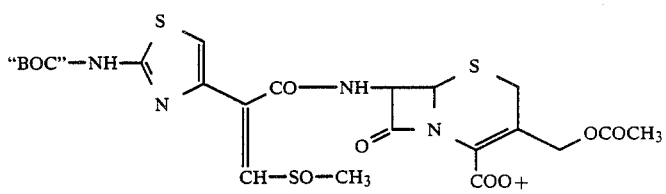

1 g of the E-isomer prepared according to Example 16 is reacted with tert.-butyl 7-aminocephalosporanate, according to the instructions of Example 4. The crude product is chromatographed over silica gel (mobile phase ethyl acetate). 320 mg of a double bond isomer are obtained, some of the NMR signals of which are split as a result of the sulphoxide isomerism.

IR (KBr): 1787, 1722, 1671, 1551, 1452, 1370, 1247, 1154, 1072, 1016 cm$^{-1}$.

NMR (CDCl$_3$): δ=9.0[2]m, 7.31/7.32[1]s, 7.24/7.17[1]s, 5.78[1]dd, J=5 Hz, J=8 Hz, 5.14/5.12[1]d, J=13 Hz, 5.07/5.03[1]d, J=5 Hz, 4.97/4.73[1]d, J=13 Hz, 3.55[1]d, J=17 Hz, 3.37[1]d, J=17 Hz, 2.88/2.82[3]s, 2.09/2.08[3]s, 1.57/1.56[9]s, 1.55[9]s ppm.

EXAMPLE 18

E-7-(2-(2-Aminothiazol-4-yl)-3-methylsulphinylprop-2-enoyl)amino-3-acetoxymethyl-3-cephem-4-carboxylic acid trifluoroacetate

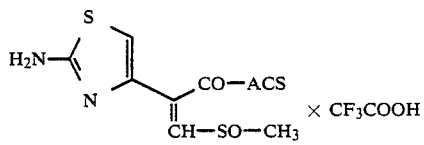

90 mg of the product from Example 17 are dissolved, at 0° C., under nitrogen, in 2 ml of trifluoroacetic acid which contain 14.4 ul of anisole. The solution is allowed to reach room temperature, and after one hour is evaporated down without heating. The residue is stirred with twice 10 ml of absolute methylene chloride, and the solution is evaporated down again. Crystallization with ether gives 40 mg of the pure product.

IR (KBr): 1772, 1723, 1665, 1525, 1379, 1232, 1064, 1025 cm$^{-1}$.

NMR (CD$_3$OD): δ=6.97[1]s, 6.71[1]s, 5.811]dd, J=4 Hz, J=5 Hz, 5.16[1]d, J=4 Hz, 5.12[1]d, J=12 Hz, 4.76[1]d, J=12 Hz, 3.70[1]d, J=18 Hz, 3.50[1]d, J=18 Hz, 2.95[3]s, 2.04[3]s ppm.

EXAMPLE 19

Z-7-(2-(2-Aminothiazol-4-yl)-3-methylsulphonylprop-2-enoyl)-amino-3-pyridiniummethyl-3-cephem-4-carboxylate

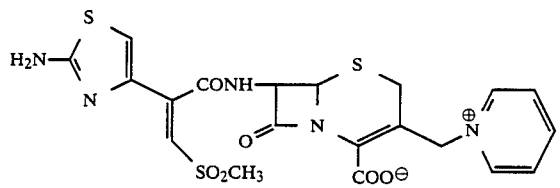

0.35 g of 1-hydroxybenzotriazole and 0.55 g of dicyclohexylcarbodiimide are added to a solution of 0.65 g of the product from Example 9 in 4.5 ml of absolute dimethylformamide, under a nitrogen atmosphere. The mixture is stirred for 4.5 hours at room temperature, and a solution of 0.75 g of 7-amino-3-pyridiniummethyl-3-cephem-4-carboxylate in 2.5 ml of water is then added. After the mixture has been stirred overnight, it is filtered off under suction from the precipitated urea, and the filtrate is evaporated down without heating. The remaining residue is taken up in water at pH 7, the solution is extracted three times with ethyl acetate, and the aqueous phase is adjusted to pH 3 with 2N hydrochloric acid and extracted again with ethyl acetate. After the aqueous phase has been adjusted to pH 7 with 2N sodium hydroxide solution and lyophilized, the title compound is separated off in pure form from the lyophilized material by chromatography. Yield 80 mg of a product which contains small amounts of the E-isomer.

IR (KBr): 1767, 1661, 1616, 1535, 1486, 1398, 1299, 1227, 1133, 1024, 970 cm$^{-1}$.

NMR (D$_2$O): δ=8.82[2]d, J=6 Hz, 8.44[1]t, J=6 Hz, 7.96[2]t, J=6 Hz, 7.00[1]s, 6.93[1]s, 5.82[1]d, J=5 Hz, 5.43[1]d, J=14 Hz, 5.25[1]d, J=14 Hz, 5.15[1]d, J=5 Hz, 3.53[1]d, J=18 Hz, 3.11[3]s, 3.09[1]d, J=18 Hz ppm.

It will be appreciated that the instant specification and examples are set forth by way of illustration and not limitation, and that various modifications and changes may be made without departing from the spirit and scope of the present invention.

We claim:

1. A compound of the formula

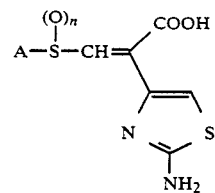

in which n is 1 or 2, and

A denotes hydroxyl, alkyl with up to 18 C atoms, which is optionally substituted by halogen, hydroxyl, C$_1$–C$_4$-alkoxy, OCOR$^2$, thio, a group a group

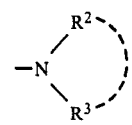

nitro, cyano, hydroxycarbonyl, C$_1$–C$_4$-alkoxycarbonyl, aminocarbonyloxy, or sulpho, wherein R$^2$ denotes branched or unbranched C$_1$–C$_4$-alkyl, m can be 0, 1 or 2 and R$^2$ and R$^3$ are identical or different and can be hydrogen, C$_1$–C$_5$-alkyl or C$_1$–C$_5$-alkanoyl, or A denotes a radical of the formula

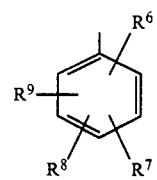

wherein

R$^6$, R$^7$, R$^8$ and R$^9$ independently of one another denote hydrogen, halogen, alkyl with up to 6 carbon atoms, aryl, a group —OCOR$^{10}$, a group

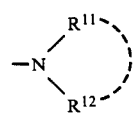

nitro, cyano, (C$_1$–C$_4$)-alkoxy (C$_1$–C$_4$)-alkyl-thio, hydroxycarbonyl, (C$_1$–C$_4$)-alkoxycarbonyl, aminocarbonyloxy, sulphonyl or sulpho, and wherein R$^{10}$ denotes branched or unbranched alkyl with up to 6 carbon atoms, and wherein R$^{11}$ and R$^{12}$ are identical or different and can be hydrogen, alkyl or alkanoyl, each with up to 6 C atoms in the alkyl part.

* * * * *

UNITED STATES PATENT AND TRADEMARK OFFICE
CERTIFICATE OF CORRECTION

PATENT NO. : 4,808,724

DATED : February 28, 1989

INVENTOR(S) : Boberg et al.

It is certified that error appears in the above-identified patent and that said Letters Patent is hereby corrected as shown below:

Col. 22, line 32    Delete "$R^2$" and substitute --$R^1$--

Signed and Sealed this

Eleventh Day of September, 1990

Attest:

HARRY F. MANBECK, JR.

*Attesting Officer*    *Commissioner of Patents and Trademarks*